(12) United States Patent
Griffin et al.

(10) Patent No.: US 8,485,992 B2
(45) Date of Patent: Jul. 16, 2013

(54) MEDICAL DEVICE HAVING SEGMENTED CONSTRUCTION

(75) Inventors: Stephen A. Griffin, San Jose, CA (US); Alain Cornil, Saint-Nom-la-Breteche (FR); Scott R. Smith, Chaska, MN (US); Lex Philip Jansen, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 86 days.

(21) Appl. No.: 12/840,091

(22) Filed: Jul. 20, 2010

(65) Prior Publication Data

US 2010/0286566 A1    Nov. 11, 2010

Related U.S. Application Data

(63) Continuation of application No. 10/446,740, filed on May 27, 2003, now Pat. No. 7,758,520.

(51) Int. Cl.
*A61M 25/09* (2006.01)
(52) U.S. Cl.
USPC .......................................... 600/585
(58) Field of Classification Search
USPC .......................................... 600/585
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,955,384 A * | 9/1990 | Taylor et al. | 600/434 |
| 5,095,915 A | 3/1992 | Engelson | |
| 5,117,838 A | 6/1992 | Palmer et al. | |
| 5,174,295 A * | 12/1992 | Christian et al. | 600/468 |
| 5,176,661 A | 1/1993 | Evard et al. | |
| 5,213,111 A | 5/1993 | Cook et al. | |
| 5,238,004 A | 8/1993 | Sahatjian et al. | |
| 5,329,923 A * | 7/1994 | Lundquist | 600/373 |
| 5,365,943 A * | 11/1994 | Jansen | 600/585 |
| 5,437,288 A | 8/1995 | Schwartz et al. | |

(Continued)

FOREIGN PATENT DOCUMENTS

| WO | 9855016 A1 | 12/1998 |
|---|---|---|
| WO | 2004068947 A2 | 8/2004 |

OTHER PUBLICATIONS

Atalar, E., "Safe Coaxial Cables," International Society for Magnetic Resonance in Medicine. 7th Scientific Meeting and Exhibition, p. 1006, SP002196325, May 22, 1999.

(Continued)

*Primary Examiner* — Sean Dougherty
*Assistant Examiner* — Michael C Stout
(74) *Attorney, Agent, or Firm* — Seager, Tufte & Wickhem, LLC

(57) ABSTRACT

A medical device having a segmented construction. In at least some embodiments, a medical device including a plurality of conductive elongated members that are of such a length and are connected together in such a manner to impart a degree of MRI compatibility to the device. In some embodiments, the elongated members can include a series of solid elongate members and tubular elongate members, which construction provides one way to control at least some properties of the device, for example, stiffness, torque transmission, flexibility, shape retention, and the like. In yet some additional embodiments, at least one of the elongated members has a recess into which a protrusion of another elongated member may fit.

19 Claims, 9 Drawing Sheets

U.S. PATENT DOCUMENTS

| | | | |
|---|---|---|---|
| 5,477,856 A * | 12/1995 | Lundquist | 600/373 |
| 5,477,864 A | 12/1995 | Davidson | |
| 5,520,194 A * | 5/1996 | Miyata et al. | 600/585 |
| 5,573,520 A | 11/1996 | Schwartz et al. | |
| 5,690,120 A | 11/1997 | Jacobsen et al. | |
| 5,693,043 A * | 12/1997 | Kittrell et al. | 606/15 |
| 5,746,701 A | 5/1998 | Noone | |
| 5,749,837 A | 5/1998 | Palermo et al. | |
| 5,769,796 A | 6/1998 | Palermo et al. | |
| 5,772,609 A | 6/1998 | Nguyen et al. | |
| 5,827,201 A * | 10/1998 | Samson et al. | 600/585 |
| 5,833,632 A | 11/1998 | Jacobsen et al. | |
| 5,853,375 A * | 12/1998 | Orr | 600/585 |
| 5,902,254 A * | 5/1999 | Magram | 600/585 |
| 5,951,494 A | 9/1999 | Wang et al. | |
| 6,001,068 A | 12/1999 | Uchino et al. | |
| 6,004,279 A | 12/1999 | Crowley et al. | |
| 6,017,319 A | 1/2000 | Jacobsen et al. | |
| 6,019,737 A | 2/2000 | Murata | |
| RE36,628 E * | 3/2000 | Sagae et al. | 148/537 |
| 6,099,485 A * | 8/2000 | Patterson | 600/585 |
| 6,139,510 A | 10/2000 | Palermo | |
| 6,165,140 A | 12/2000 | Ferrera | |
| 6,165,292 A * | 12/2000 | Abrams et al. | 148/563 |
| 6,248,082 B1 | 6/2001 | Jafari | 600/585 |
| 6,280,539 B1 * | 8/2001 | Abrams et al. | 148/402 |
| 6,290,656 B1 * | 9/2001 | Boyle et al. | 600/585 |
| 6,327,492 B1 * | 12/2001 | Lemelson | 600/434 |
| 6,409,683 B1 | 6/2002 | Fonseca et al. | |
| 6,428,489 B1 | 8/2002 | Jacobsen et al. | |
| 6,436,056 B1 | 8/2002 | Wang et al. | |
| 6,451,026 B1 * | 9/2002 | Biagtan et al. | 606/108 |
| 6,458,088 B1 | 10/2002 | Hurtak et al. | |
| 6,508,803 B1 | 1/2003 | Horikawa et al. | |
| 6,673,025 B1 * | 1/2004 | Richardson et al. | 600/585 |
| 6,682,493 B2 * | 1/2004 | Mirigian | 600/585 |
| 6,799,067 B2 * | 9/2004 | Pacetti et al. | 600/431 |
| 6,845,259 B2 * | 1/2005 | Pacetti et al. | 600/407 |
| 6,918,882 B2 | 7/2005 | Skujins et al. | |
| 6,921,397 B2 * | 7/2005 | Corcoran et al. | 604/535 |
| 6,993,373 B2 | 1/2006 | Vrijheid et al. | |
| 7,001,345 B2 | 2/2006 | Connors et al. | |
| 7,074,197 B2 | 7/2006 | Reynolds et al. | |
| 2002/0019599 A1 * | 2/2002 | Rooney et al. | 600/585 |
| 2002/0032390 A1 * | 3/2002 | Jafari | 600/585 |
| 2002/0058888 A1 * | 5/2002 | Biagtan et al. | 600/585 |
| 2003/0028127 A1 * | 2/2003 | Balzum et al. | 600/585 |
| 2003/0105415 A1 * | 6/2003 | Mirigian | 600/585 |
| 2004/0039304 A1 * | 2/2004 | Connors et al. | 600/585 |
| 2004/0167438 A1 * | 8/2004 | Sharrow | 600/585 |
| 2007/0112282 A1 * | 5/2007 | Skujins et al. | 600/585 |

OTHER PUBLICATIONS

Konings, M.K. et al., "Catheters and guidewires in interventional MRI: problems and solutions," Medica Mundi, 45 (1):31-39, Mar. 2001.

Konings, M.K. et al., "Heating Around Intravascular Guidewires by Resonating FR Waves," Journal of Magnetic Resonance Imaging, 12:79-85, 2000.

Liu, C.Y. et al., "Safety of MRI-Guided Endovascular Guidewire Applications," Journal of Magnetic Resonance Imaging, 12(1):75-78, Jul. 2000.

Poutsma, A., "Regulatory processes necessary to commercialize a seizure prediction technology promises and pitfalls of biosignal analysis: seizure prediction and management (case study)," 2001 Conference Proceeding of the 23rd Annual International Conference of IEEE Engineering in Medicine and Biology Society.

Yang, X. et al., "Thermal effect of intravascular MR imaging using an MR imaging-guidewire: An in vivo laboratory and histopathological evaluation," Medical Science Monitor—International medical journal of experimental and clinical research (Poland) Jul. 2002, 8(7)pMT113-7, ISSN 1234-1010 Journal code: 9609063.

Yeung, C.J. et al., "Modeling of RF Heating Due to Metal Implants in MRI," 2002 IEEE Antennas and Propagation Society International Symposium, Digest, vol. 1:823-826, 2002.

Yeung, et al., "FR safety of wires in interventional MRI: using a safety index," Magn Reson Med, 47(1): 187-93, Jan. 2002.

* cited by examiner

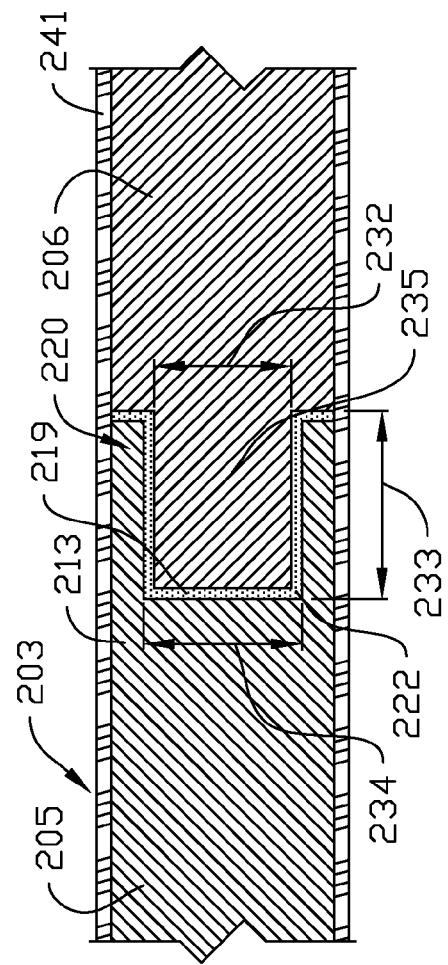
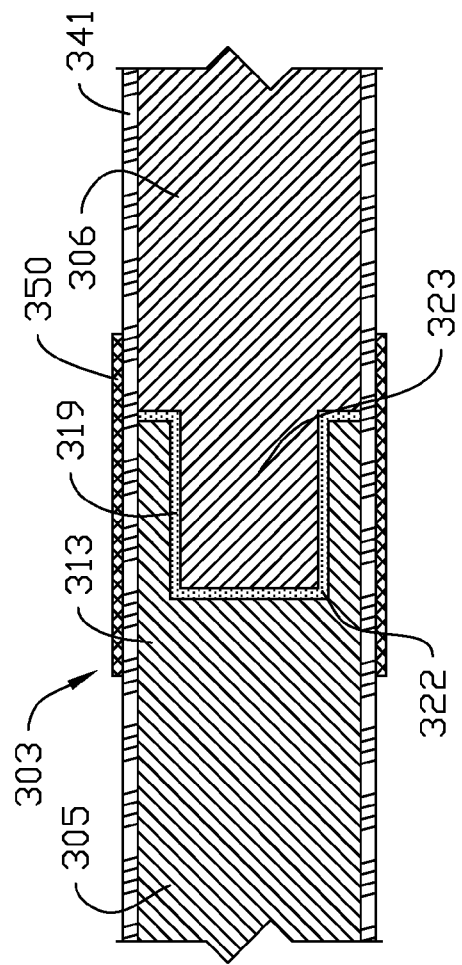
Fig.4
Fig.5

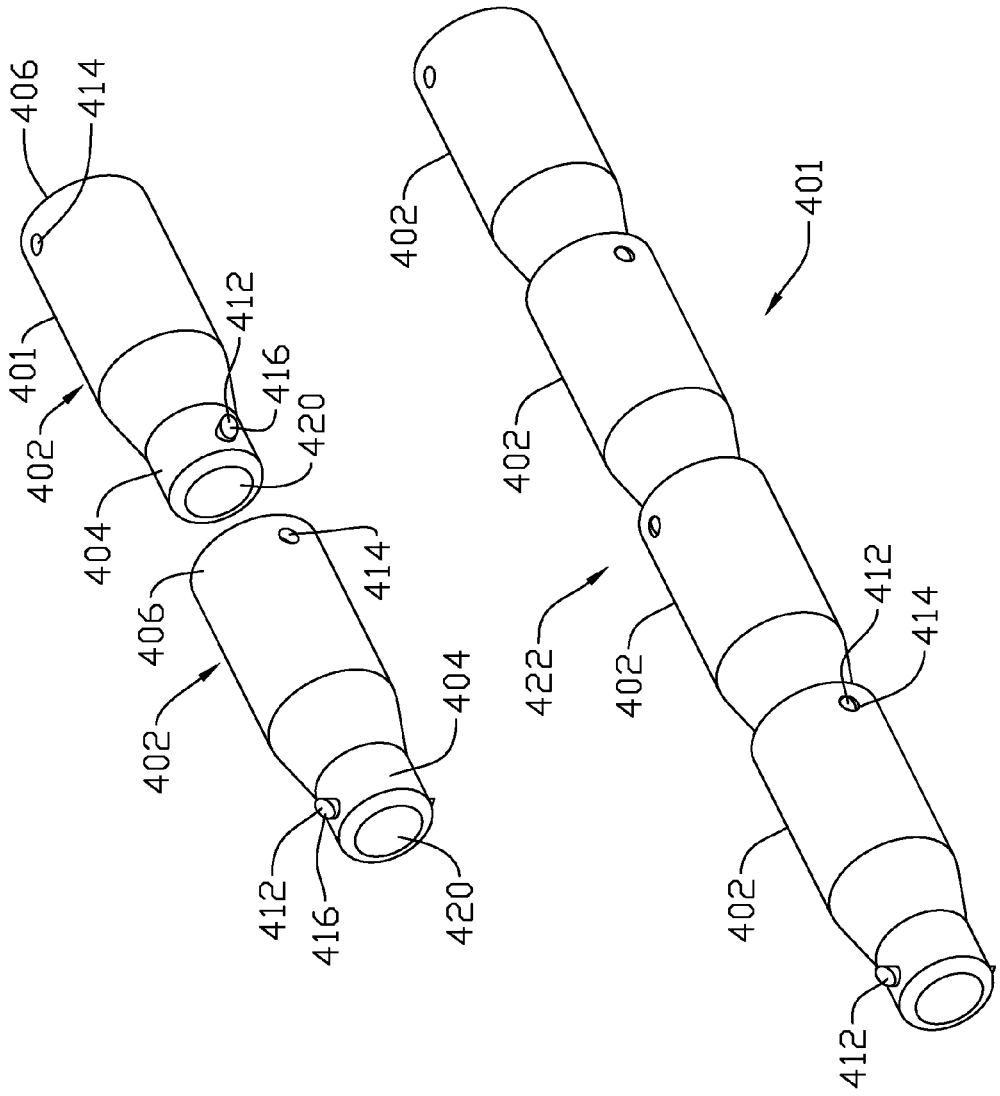

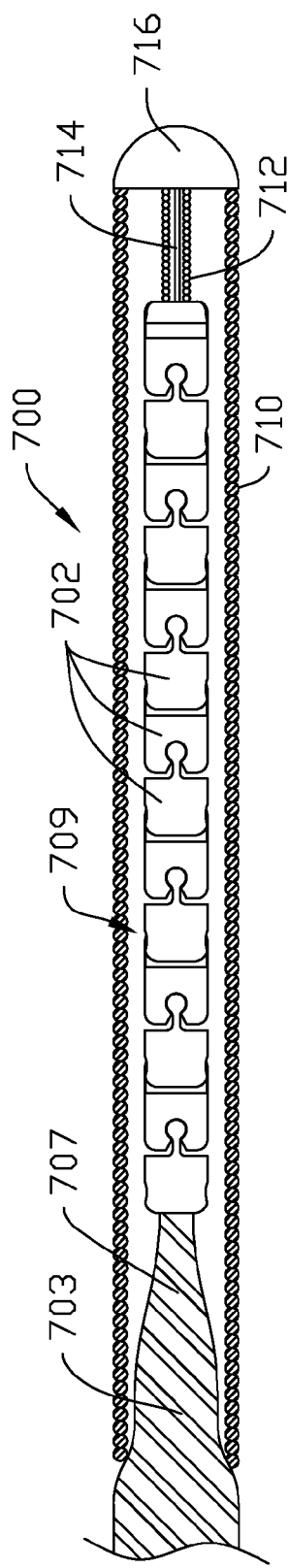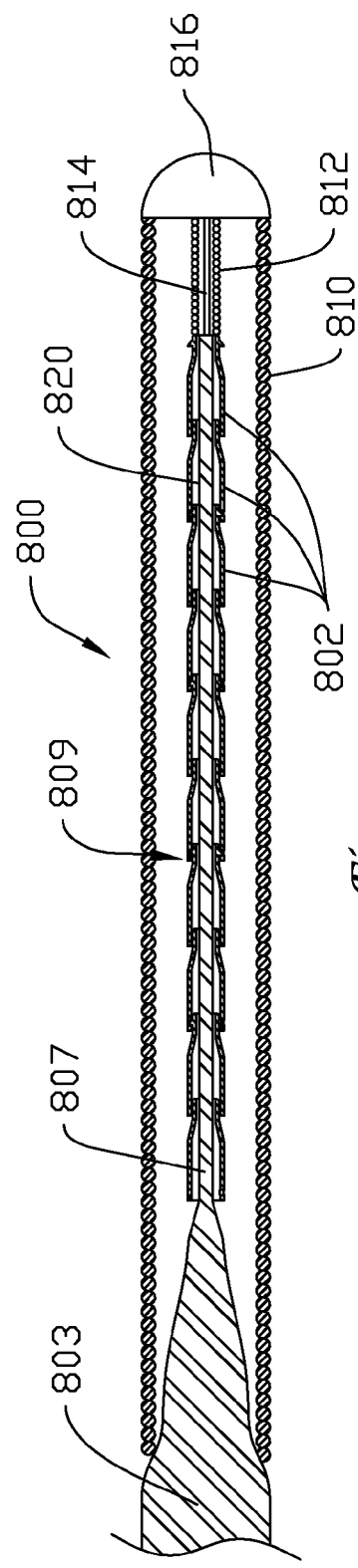

MEDICAL DEVICE HAVING SEGMENTED CONSTRUCTION

CROSS-REFERENCE TO RELATED APPLICATIONS

This application is a continuation of U.S. application Ser. No. 10/446,740 filed May 27, 2003, the entire disclosure of which is incorporated herein by reference.

FIELD OF THE INVENTION

The invention relates generally to medical devices and more particularly to a medical device that may be used with magnetic resonance imaging systems or may have a superior combination of torque, stiffness and flexibility characteristics.

BACKGROUND

A wide variety of medical devices, for example, guidewires, catheters, and the like have been developed for medical use, for example, intravascular use. Some such devices are used in conjunction with imaging techniques to aid a user in locating the device, for example, within the body of a patient. A number of different medical devices and assemblies are known, each having certain advantages and disadvantages. There is an ongoing need to provide alternative medical device structures and assemblies.

SUMMARY OF SOME EMBODIMENTS

The invention provides several alternative designs, materials and methods of manufacturing alternative medical device structures and assemblies.

In at least some embodiments, the invention relates to a medical device, for example, a guidewire, a catheter, or the like, including a plurality of elongated members connected together. Some example embodiments pertain to medical devices that may include a plurality of electrically conductive elongate members, each member being of a length less than that of one half of a wavelength of radio waves that an MRI machine may use. In some embodiments, each adjacent pair of conductive elongate members is connected in a suitable manner to impede electrical current flow from one elongated member to the next, thus imparting the device a degree of compatibility for use with the MRI machine. For example, the elongate members may be connected to each other using a joint having a relatively high electrical resistance or which is relatively non-conductive in relation to the conductive elongate members. For example, in some embodiments a low or non-conductive adhesive can be used to connect the elongate members; however, other connection mechanisms having relatively high electrical resistance or relatively low conductivity can be used. In some embodiments, two or more conductive members may be connected by a third member having relatively high electrical resistance or having a low electrical conductivity relative to the conductivity of the conductive members being connected. Additionally, some embodiments relate to several alternative designs, materials and methods of manufacturing alternative components and connection structures for use in a medical device.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 4 is a partial longitudinal cross sectional schematic view of another example embodiment of a joint construction that may be used in a medical device;

FIG. 5 is a partial longitudinal cross sectional schematic view of another example embodiment of a joint construction that may be used in a medical device including a shield;

FIG. 6 is an exploded perspective view of another example embodiment of a joint construction that may be used in a medical device showing two elongated segments adapted to be connected together;

FIG. 7 is a perspective view of an example embodiment of a part of a medical device including a plurality of elongated segments as shown in FIG. 6 that are connected together;

FIG. 12 is a cross-sectional schematic view of an example embodiment of a guidewire including a distal portion that includes a plurality of segments as shown in FIG. 8 that are connected together;

FIG. 13 is a cross-sectional schematic view of an example embodiment of a guidewire including a distal portion that includes a plurality of segments as shown in FIG. 6 that are connected together.

Figure 1:
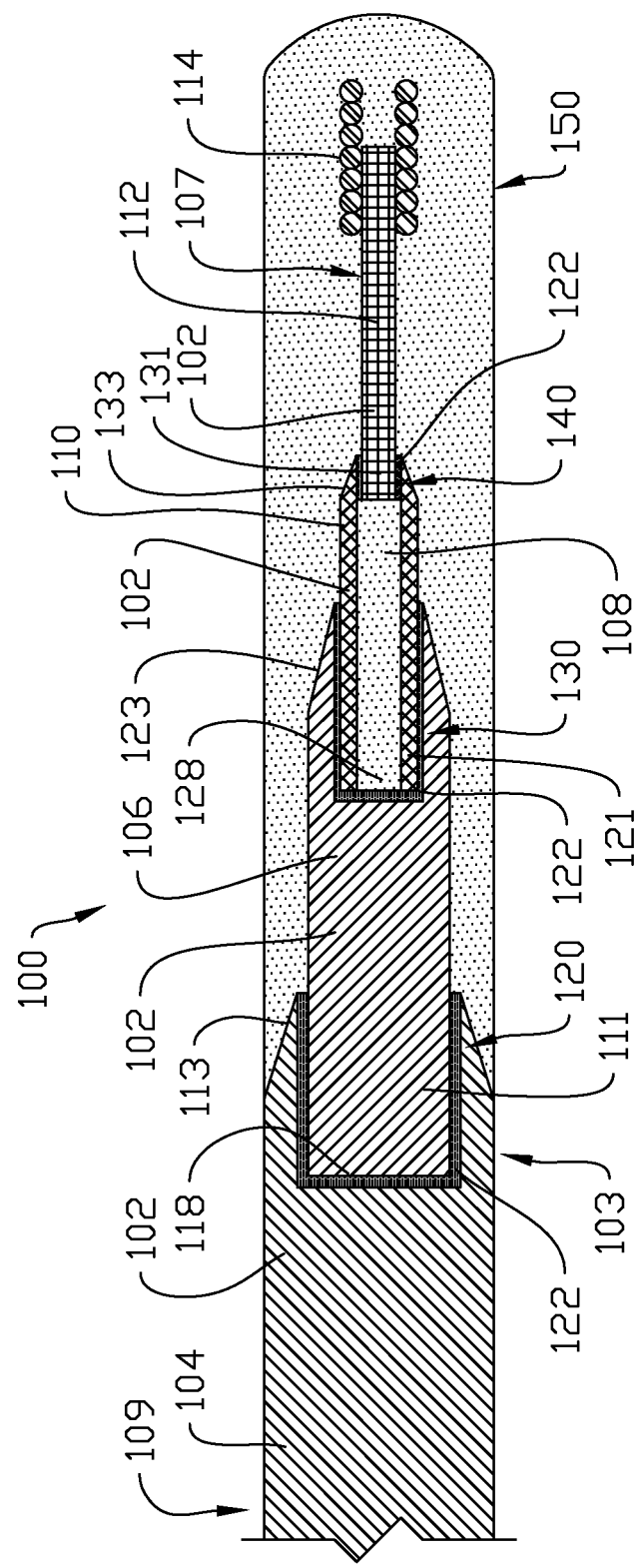
FIG. 1 is a longitudinal cross sectional schematic view of an example embodiment of a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

The following description should be read with reference to the drawings wherein like reference numerals indicate like elements throughout the several views. The detailed description and drawings illustrate examples of various embodiments of the claimed invention, and are not intended to be limiting.

At least some embodiments of the invention provide a medical device, or components or structures for use in a medical device, that include two or more elongated structural elements that are connected. In some embodiments, a degree of MRI compatibility is imparted into the device. For example, in certain embodiments, at least some of the conductive elements of the device have a length less than that of one half of a wavelength of radio waves that a MRI machine may use. Additionally, in at least some embodiments, a pair of elongated conductive elements are connected in such a manner as to impede electrical current flow from one elongated member to the next.

At least some embodiments provide a joint configuration for connecting elongated elements. For example, a first elongate member may have a recess in one end and a second elongate member may have a protrusion on one end that is adapted and configured to fit into the recess. In some embodiments, the joint may include an elongate member or segment made of a material having a low electrical conductivity relative to the conductivity of the elongated elements being connected.

Although set forth with specific reference to guidewires in the example embodiments shown in the Figures and discussed below, the invention may be applicable to almost any intracorporal medical device having an elongated structure made up of two or more adjacent or consecutive elongated members or sections that are connected together. For example, the invention may be applicable to elongated shafts, for example hypotube shafts and the like, for medical catheters (e.g., guide catheters, diagnostic catheters, rapid exchange balloon catheters, stent delivery catheters, over-the-wire catheters, etc.) or drive shafts for medical devices (atherectomy catheters, IVUS catheters, intravascular rotational devices, etc.), and the like, or other such medical devices.

Refer now to FIG. 1, which illustrates a partial longitudinal cross sectional view of a medical device 100, which is a guidewire, in accordance with one embodiment. The guidewire 100 generally includes an elongated shaft 103 having a distal end portion 107 and a proximal end portion 109, and including a plurality of elongate members 102, for example elongate members 104, 106, 110 and 112. It should be understood that the number of elongate members can vary, as is appropriate for the particular application and desired length and characteristics of the guidewire. Each of the elongated members 112 can include any suitable structure for use as members for the particular medical device constructed, such as a wire, a tube, a braid, a coil, and the like. Each of the elongated members 102 can have a solid cross-section, a hollow cross-section, or can include a combination of sections or portions having solid cross-sections and hollow cross sections. In the embodiment shown, the elongate members 104, 106 or 112 have a generally solid cross section, and elongate member 110 is a generally tubular member having a lumen 108 extending therethrough. Elongated members 102 are joined or connected in a suitable manner to form the shaft 103. In the embodiment shown, the elongated members 102 are connected together in such a manner and are of such a length to impart a degree of MRI compatibility to the device, as discussed in more detail below, however this is not necessarily required in all embodiments.

The elongate members 102 can be continuously tapered, can have a tapered or beveled section or a number or series of tapered or beveled sections of differing diameters, or can have a constant diameter. In some embodiments, the entire shaft 103, or portions thereof, is tapered or otherwise formed to have a geometry that decreases in cross sectional area toward the distal end thereof. For example, the elongate members 102 disposed distally may have a smaller outer diameter, as is depicted in this figure. If tapered, each elongated member individually, or in combination, or the shaft 103 as a whole can include a uniform or a non-uniform transition of the sections, depending on the transition characteristics desired. For example, each elongated member individually, or in combination, or the shaft 103 as a whole may be linearly tapered, tapered in a curvilinear fashion, or tapered in a step-wise fashion. The angle of any such tapers can vary, depending upon the desired flexibility, stiffness, or other characteristics. The length of the taper may be selected to obtain a more (longer length) or less (shorter length) gradual transition in stiffness. The number of tapers or bevels may also vary, as is appropriate for the particular application.

The structure used to construct shaft 103 can be designed such that the proximal portion thereof is relatively stiff for pushability and torqueability, and the distal portion thereof is relatively flexible by comparison for better lateral trackability and steerability. As used herein, the proximal portion and the distal portion may generically refer to any two adjacent sections or portions along any portion of the shaft. For example, in some embodiments, the more proximal elongated member or members can have a constant or generally uniform diameter along its length to enhance stiffness. However, embodiments including a proximal portion having a tapered portion or a series of tapered portions are also contemplated. The diameter of the proximal portion of shaft 103 is sized appropriately for the desired stiffness characteristics dependent upon the material used. For example, in some embodiments, the proximal portion can have a diameter in the range of about 0.010 to about 0.025 inches or greater, and in some embodiments, in the range of about 0.010 to about 0.018 inches or greater.

The more distal elongated member or members of the shaft 103 can likewise be constant diameter, can be continuously tapered, or can have a tapered section or a number or a series of tapered sections of differing diameters. In embodiments where the structure of shaft 103 is designed such that the distal portion is relatively flexible by comparison to the proximal portion, the distal portion typically does include at least one tapered or reduced diameter portion for better flexibility characteristics.

The elongated members 102 can be made of any suitable material including, for example, metals, metal alloys, polymers, or the like, or combinations or mixtures thereof. Some examples of suitable metals and metal alloys include stainless steel, such as 304V, 304L, and 316L stainless steel; alloys including nickel-titanium alloy such as linear elastic or super-elastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); Elgiloy; Hastelloy; Monel 400; Inconel 625; or the like; or other suitable material.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Within the family of commercially available nitinol alloys, is a category designated "superelastic" (i.e. pseudoelastic) and a category designated "linear elastic" which, although may be similar in chemistry, can exhibit distinct and useful mechanical properties. Some examples of nickel titanium alloys can be found in U.S. Pat. Nos. 5,238,004 and 6,508,803, which are herein incorporated by reference. One example of a suitable nickel-titanium alloy is FHP-NT alloy commercially available from Furukawa Techno Material Co. of Kanagawa, Japan.

The elongated members 102 along the entire shaft 103 can be made of the same material, or in some embodiments, some or all can be made of or include portions or sections that are made of different materials. In some embodiments, the material used to construct certain elongated members 102 are chosen to impart varying characteristics, such as flexibility and stiffness, to different portions of shaft 103. Therefore, each of elongate members 102 may comprise one or more materials that enhance such desired characteristics. For example, more proximal elongated members may be formed of different materials (i.e., materials having different moduli of elasticity) resulting in a difference in flexibility. In some embodiments, the material used to construct the more proximal members can be relatively stiff for pushability and torqueability, and the material used to construct the more distal members can be relatively flexible by comparison for better lateral trackability and steerability. For example, more proximal elongated members can be formed of a high modulus of elasticity material, for example, stainless steel, and the more distal elongated members can be formed of, for example, a superelastic (i.e. pseudoelastic) or linearelastic alloy (e.g., nitinol) material.

In one particular example embodiment in accordance with FIG. 1, the elongated member 104 is an elongate solid wire made of a high modulus material, such as stainless steel, the elongated member 106 is an elongate solid wire made of a more elastic material, such as superelastic (i.e. pseudoelastic) or linearelastic nitinol, the elongated member 110 is an elongated tube defining a lumen 108, and is made of a more elastic material, such as superelastic (i.e. pseudoelastic) or linearelastic nitinol, and the elongate member 112 is an elongate solid wire made of a shapeable material, such as Elgiloy.

To enhance compatibility with Magnetic Resonance Imaging (MRI) machines, it may be desirable to make the guidewire 100, or portions thereof, in a manner that embodies certain characteristics. For example, the shaft 103, or portions thereof, such as one or more of the elongated members 102, may be made of a material that does not substantially distort the image and create substantial artifacts (artifacts are gaps in the image). Certain ferromagnetic materials, for example, may not be suitable because they may create artifacts in an MRI image. The shaft 103, or portions thereof, may also be made from a material that the MRI machine can image. Some materials that exhibit these characteristics include, for example, tungsten, Elgiloy, MP35N, nitinol, and others.

The material and/or structure used to create the shaft 103 can also be such that the influence of the magnetic field from the MRI machine on the shaft 103 will not generate undue heat in the shaft 103, or other portions of the medical device. If conductors of sufficient length are present in an RF field generated by an MRI machine, heating can occur by resonating RF waves along the conductors. If such resonance occurs, the incident RF wave is bounced back at the end points of the structure, causing the reflected RF waves to travel back and forth along the longitudinal axis of the structure, in a way that standing RF waves are formed. The occurrence of such resonance, and the heat generated thereby, can be reduced in a number of different ways. For example, in some embodiments, one or more of the elongated members 102 within the shaft 103, or other portions of the guidewire, can be made of relatively low conductive materials that will not generate significant heat when used with an MRI machine.

However, in embodiments where one or more of the elongated members 102 is made of a relatively conductive material, such conductive elongated members can be designed to have a length that is less than one half of the wavelength, and in some embodiments, less than one quarter the wavelength, of the radio waves that are generated by the MRI machine being used. It has been found that by providing the conductive elongated members with such lengths can reduce the amount of resonance, and thereby reduce the amount of heat generated. The length of the elongated members 102 may be also influenced by the length and flexibility characteristics desired in the shaft 103 as well as by desired MRI compatibility. As indicated above, in some embodiments, at least some of the elongate members typically have a length of less than one half of the wavelength, and in some embodiments, less than one quarter the wavelength, of the radio waves that are generated by the MRI machine being used. In some embodiments, such lengths can range from about 25 cm or less, such as in the range of about 3 to about 21 cm, or in the range of about 10 to about 21 cm. It should be understood, however, that these lengths may vary, depending upon the wavelength of the RF waves generates by a particular MRI machine.

The total length of the shaft can vary, and is often dependent upon the desired characteristics, and, of course, the desired use of the medical device. In some embodiments, the shaft can have a length that is adapted such that when the distal end of the medical device is navigated within the anatomy to a designated target site, the proximal end of the device can extend out of the patients body, for example, for manipulation by an operator. In some embodiments, the shaft 103 has a length in the range of about 30 to about 350 centimeters. The number of elongate segments can also vary, as is appropriate for the particular application and desired length of the shaft. Three, four, five or more elongated members may be required to make a shaft of appropriate length and characteristics.

Additionally, in embodiments where two conductive elongated members 102 are to be connected together, such members can be connected using a connection mechanism that acts to impede or interrupt electrical conductivity or electrically insulate the two members from one another, thereby retarding the occurrence of a conductive path having a length that is the same or greater than one half of the wavelength of the radio waves that the MRI machine generates. Depending on the range of wavelengths a particular MRI machine generates, this length may vary.

For example, some MRI machines may use a frequency of approximately 64 Mhz, with a corresponding wavelength generated in certain media of approximately 50 cm or greater. If MRI compatibility is desired and heat generation through resonance is to be reduced, conductive paths in the guidewire can be less than about 25 cm, which is one half of the approximately 50 cm wavelength generated by the MRI machine. Therefore, the length of each of the conductive elongated members 102 in such a guidewire can be less than about 25 cm, and low conductivity connection mechanisms can be used to connect the conductive elongated members to retard the occurrence of a conductive path between conductive members that would have a length that is 25 cm or greater. Additionally, in some embodiments, it may be useful to provide the length of each of the conductive elongated members 102 be less than about 25 cm, for example, about 21 cm or less, to better ensure the reduction of the likelihood of resonance occurring.

In some embodiments, the connection mechanism for connecting two elongated members is a relatively low conductive joint, such as joints 120, 130 and 140, which are provided between the two adjacent elongate members 102. Such joint may include structure and materials to provide a suitable bond or link to connect two elongate members, and to substantially retard, reduce, and/or prevent the flow of electrical current from one elongated member to the next. Such joints may include a mechanical mechanism, an adhesive or bonding mechanism, or the like, for connecting the two members together. Some suitable connection techniques include the use of adhesive bonding, thermal bonding, crimping, swaging, mechanical interlocking, or other suitable attachment techniques, or combinations thereof. Additionally, in some cases, techniques such as welding, brazing, soldering, or other such suitable attachment techniques, or combinations of any of these can be used in constructing a joint. Such joints can incorporate separate joining members or materials, can utilize the structure of the elongated members to create the joint, or a combination thereof.

Such joints can also include the use of relatively non-conductive material to electrically insulate the two connected elongated members from each other. In some embodiments, all or part of the connection mechanism or material is made of relatively non-conductive or insulative material. In some other embodiments, relatively non-conductive or insulative material or members can be distinct or separate from the connection mechanism or members, but still act to prevent the flow of electrical current from one elongated member to the next. For example, in some embodiments, the joint may include a mechanical spacer that creates a uniform gap between the two elongate members. This spacer may be made from a suitable non-conductive material, for example nylon, Kevlar, or other relatively non-conductive material. In some embodiments, the joint can be constructed to create a gap or space between the two elongate members to thereby provide electrical path resistance. Additionally, in some embodiments, the joint may include an elongated member made of a relatively non-conductive material that connects the two relatively conductive elongated members together.

Some particular embodiments use a relatively non-conductive adhesive or bonding material in combination with mechanical interlocking of the elongated members to create a joint. For example, in one particular embodiment in accordance with FIG. 1, the elongated member 104 is an elongate solid wire that has a beveled distal portion 113 and a recess 118 formed in the distal portion. The elongated member 106 is an elongate solid wire having a proximal portion 111 that is adapted and configured to fit at least partially within the recess 118 in the distal end of the first portion 104. A relatively non-conductive adhesive or bonding material 122 is disposed between the inner surface of the recess 118 and the outer surface of the proximal portion 111 of the elongated member 106 to provide a relatively low conductive joint 120 between two elongate members 104 and 106. Similarly, the elongated member 106 has a beveled distal portion 123 and a recess 128 formed in the distal portion thereof, and elongated member 110 includes a proximal portion 121 that is adapted and configured to fit at least partially within the recess 128 in the distal end of the elongated member 106. Again, a relatively non-conductive adhesive or bonding material 122 is disposed between the inner surface of the recess 128 and the outer surface of the proximal portion 121 of the elongated member 110 to provide a relatively low conductive joint 130 between two elongate members 106 and 110. The elongated member 110 is an elongated tube having a beveled distal portion 133, and defines a lumen 108. Elongated member 112 is an elongate solid wire having a proximal portion 131 that is adapted and configured to fit at least partially within the distal end of the lumen 108. Again, a relatively non-conductive adhesive or bonding material 122 is disposed between the inner surface of the lumen 108 and the outer surface of the proximal portion 131 of the elongated member 112 to provide a relatively low conductive joint 120 between two elongate members 110 and 112. In this embodiment, each of the elongated members 102 is of a length that is less than half the wavelength of the radio waves of an MRI machine with which the guidewire is intended for use.

It should also be noted that the use of elongated members having a generally solid cross section, such as members 104, 106, and 112 in combination with elongated members having a generally tubular cross section, such as member 110, can, in some embodiments, provide a benefit in the construction. For example, such medical devices that are constructed from a series of solid elongate members and tubular elongate members provides a way to easily control at least some properties of the device, for example, stiffness, torque transmission, flexibility, shape retention, and the like. For example, a tubular member having a lumen therein that forms an unfilled space within the member can have substantially different characteristics than a solid member having a similar outer diameter. In some embodiments, the lumen of a tubular member used in the construction can have at least 50% or more of the lumen remain unfilled. It should also be understood that in other embodiments, more than one tubular elongated member can be used, depending upon the desired characteristics of the final device. Additionally, the arrangement of the solid and tubular members can also be varied, depending upon the desired characteristics.

The adhesive or bonding material 122, or other such structure or material used to create these joints 120, 130, and 140, can include any material capable of providing a suitable bond or joining force between the elongated members 102, and which has a relatively low level of conductivity relative to at least some of the elongated members 102. In at least some embodiments, the relatively non-conductive adhesive or bonding material 122, or other relatively non-conductive material or structure used to electrically insulate two connected elongated members from each other has a relatively low dielectric constant. For example, in some embodiments, the adhesive or bonding material 122, or other such material or structure has a dielectric constant in the range of about 5 or less, and in some embodiments, in the range of about 2 to about 4. Some examples of materials which may exhibit both adhesive and relatively non-conductive characteristics include adhesives comprising cyanoacrylate, epoxy, acrylate, silicone, urethane or the like.

Furthermore, an adhesive or bonding material with a high loss tangent may also be used, and may help to dissipate energy along the length of the wire. This could be accomplished, for example, through the addition of a small amount of filler, such as carbon, silver, gold, titanium, tantalum, tungsten, ionic materials, and the like, to the bonding material. This could also be accomplished through the use of bonding material that includes or is made of ionomers, such as ionic polymers, and the like. In some embodiments, an adhesive or bonding material having a conductivity in the range of about 1 to about $10^4$ siemens/m can be used. The loss tangent can be calculated using conductivity value. In some embodiments, the material can be engineered to have the desired such properties taking into account the frequency used in the MRI machine.

Additionally, in some embodiments, the size and structure of one or more of the joints, such as 120 or 130, is engineered such that it has a relatively low capacitance in the environment in which they are intended for use. For example, in some embodiments, the joints are engineered to have a capacitance in the range of about 10 Pico Farad or less, and in some embodiments, in the range of about 5 Pico Farad or less. Furthermore, in some embodiments, the size and structure of one or more of the joints, such as 120 or 130, is engineered such that it has a relatively a high reactance in the environment in which they are intended for use for reduction of resonance. For example, in some embodiments, the joints are engineered to have a reactance in the range of about 100 Ohms or greater, and in some embodiments, in the range of about 400 Ohms or greater.

The guidewire 100 may also include additional structure, such as a sleeve, sheath, tube, coil, marker member, or the like, disposed on, in, over, or adjacent at least a portion of the shaft 103. For example, in the embodiment shown in FIG. 1, a coil 114 is disposed on the distal end of the elongated member 112. Such a coil 114 can serve as a shaping or safety structure, as a radiopaque marker member, or as structural support, and the like.

The coil 114, or other portions of the guidewire can include, be made of, be plated with, or be doped with, a marker member or material to make the guidewire, or portions thereof, more visible when using certain imaging techniques, for example, MRI, fluoroscopy, and other such techniques. Radiopaque materials are understood to be materials capable of producing a relatively bright image on an MRI or fluoroscopy screen or another imaging technique during a medical procedure. This relatively bright image aids the user of device in determining its location. Some examples of radiopaque materials suitable for use with MRI include tungsten, tantalum, gold, platinum, plastic material loaded with such a radiopaque filler, and others, or the like. Some examples of radiopaque materials suitable for use with fluoroscopy can include gold, platinum, palladium, tantalum, tungsten, tungsten alloy, plastic material loaded with such a radiopaque filler, for example barium subcarbonate powder, and the like, or combinations, alloys, or mixtures of any such materials and the like. In some embodiments, it is also contemplated that a separate additional radiopaque member or a series of radiopaque members, such as coils, bands, tubes, or other such structures could be attached to or incorporated on or within the medical device, or incorporated into shaft 103 by material selection for the shaft, or by plating, drawing, forging, cladding, or other metal implantation techniques.

The embodiment shown in FIG. 1 also includes an outer member 150 which is a sheath, such as a polymer sheath, disposed over the distal portion of the shaft 103. Suitable material for use as the sheath include any material that would give the desired adhesion, flexibility or other desired characteristics. Some examples of suitable materials can include polymers, and like materials. Some examples of suitable polymers include, but are not limited to, polyurethane, polyethylene, polyamide, elastomeric polyamides, silicones, polyether-ester (for example, a polyether-ester available under the trade name HYTREL), block copolymer such as polyether block amide (PEBA) (for example that available under the trade name PEBAX®), or mixtures, combinations, or copolymers thereof. Outer member 150 may be a single polymer, multiple layers, or a blend of polymers. The outer member 150 may be shaped to maintain a constant outer diameter of the guidewire, as shown, or may be shaped or tapered to achieve desired characteristics. In some embodiments, the sheath or other outer member can include different sections made of different materials, or having different moduli of elasticity, or having different amounts of loading with certain materials, such as radiopaque material, and the like.

Additionally, in some embodiments, a coating, for example a lubricious (e.g., hydrophilic) or other type of coating may be applied over portions or all of the guidewire 100. Hydrophobic coatings such as fluoropolymers provide a dry lubricity which improves the handling of medical devices and device exchanges. Lubricious coatings improve steerability and improve lesion-crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

FIGS. 2A-3D and the discussion below illustrate and describe some additional examples of suitable joint configurations.

Figure 2A:
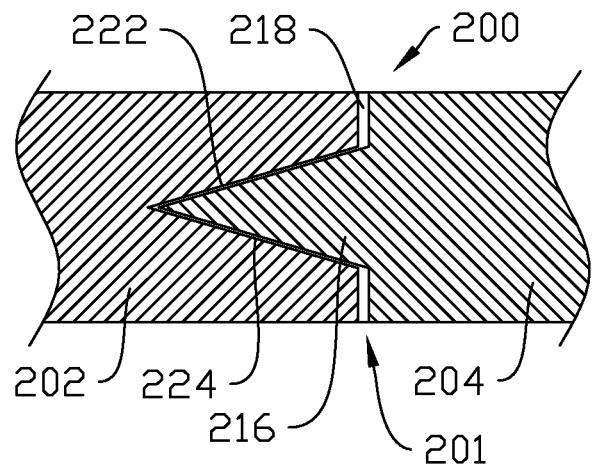
FIG. 2A is a partial longitudinal cross sectional schematic view of another example embodiment of a joint construction that may be used.

Turn now to FIG. 2A, which is a partial longitudinal cross sectional view of a guidewire shaft 200 showing a joint between elongate member 202 and elongate member 204. In this embodiment, recess 218 of elongate member 202 is defined by two angled walls 222 and 224 that connect to form a triangular shaped recess 218. The protrusion 216 of elongate member 204 is adapted to fit within this recess 218. A gap between elongate member 202 and 204 may be desired to help electrically insulate the two elongate members from each other, and prevent the flow of current between the two members. This gap may be filled with adhesive or bonding material, for example, a relatively non-conductive adhesive or bonding material, as was discussed above. This gap may also include a spacer such as a nylon or Kevlar spacer, for example, to ensure the gap is uniform or to enhance other characteristics of the joint.

Figure 2B:
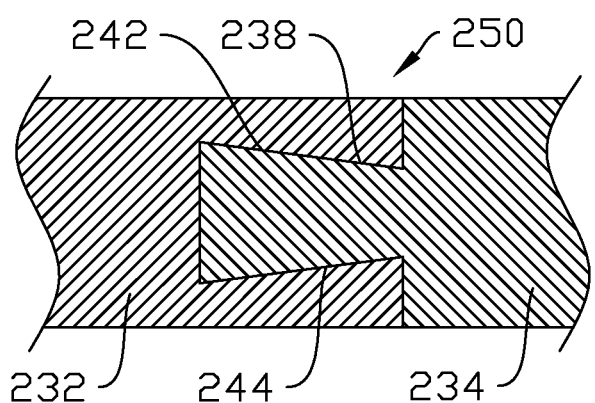
FIG. 2B is a partial longitudinal cross sectional schematic view of an example embodiment of a joint construction that may be used in a medical device.

FIG. 2B is a partial longitudinal cross sectional view of a guidewire shaft 250 showing a joint between elongate member 232 and elongate member 234. In this embodiment, recess 238 of elongate member 232 is defined by two angled walls 238 and 234 that connect to form a dovetail shaped recess 238. The protrusion 236 of elongate member 234 is adapted to fit within this recess 238. Again, a gap between elongate member 232 and 234 may be desired to help electrically insulate the two elongate members from each other, and prevent the flow of current between the two members. This gap may be filled with adhesive or bonding material, for example, a relatively non-conductive adhesive or bonding material, as was discussed above. This gap may also include a spacer such as a nylon or Kevlar spacer, for example, to ensure the gap is uniform or to enhance other characteristics of the joint.

Turn now to FIGS. 3A, 3B, 3C, and 3D, which are cross sectional views of some additional example joint constructions. These cross sections are of the joints between elongate members showing that elongate members can have recesses and/or protrusions that may have a variety of shapes, of which only a few of which are depicted in these Figures.

Figure 3A:
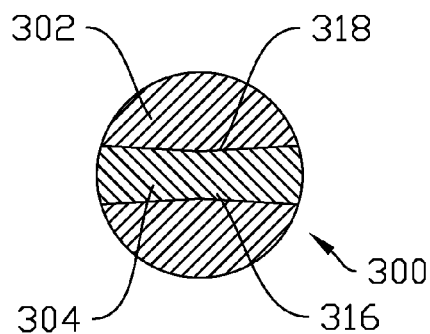
FIG. 3A is a cross sectional schematic view of another example embodiment of a joint construction that may be used in a medical device.
Figure 3B:
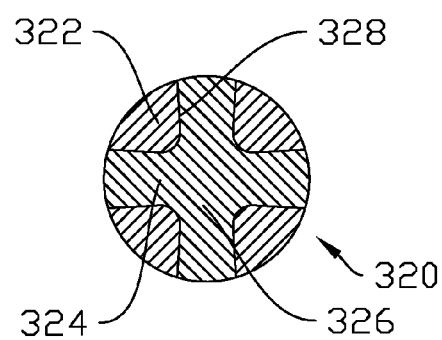
FIG. 3B is a cross sectional schematic view of another example embodiment of a joint construction that may be used in a medical device.
Figure 3C:
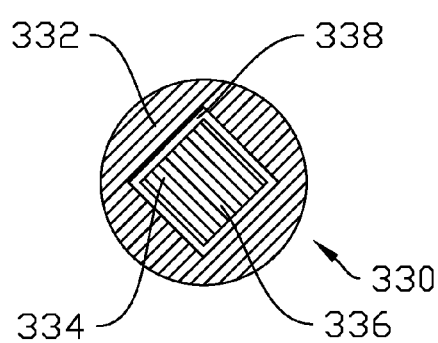
FIG. 3C is a cross sectional schematic view of another example embodiment of a joint construction that may be used in a medical device.
Figure 3D:
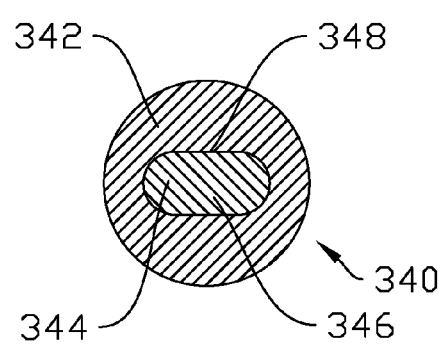
FIG. 3D is a cross sectional schematic view of another example embodiment of a joint construction that may be used in a medical device.

For example, in FIG. 3A elongate member 302 includes a recess 318 that may be generally slot-shaped, and the elongated member 303 includes a protrusion 316 that generally is generally configured to fit within the slot-shaped recess 318. In FIG. 3B, elongate member 322 includes a recess 328 that may be generally cross-shaped, and the elongated member 323 includes a protrusion 326 that is generally configured to fit within the cross-shaped recess 328. In FIG. 3C, elongate member 332 includes a recess 338 that may be generally may be formed from a closed curve, for example, the regular polygon shown, and the elongated member 333 includes a protrusion 336 that is generally configured to fit within the closed curve regular polygon-shaped recess 338. In FIG. 3D, elongate member 342 includes a recess 348 that may be generally formed from a closed curve, for example, the curved shape shown, and the elongated member 343 includes a protrusion 346 that is generally configured to fit within the curve-shaped recess 348. The generally non-circular recesses and protrusions shown in these figures have the advantage of enhancing the torque transmission from one elongate member to the other. Non-circularity, however, is not necessary. For example, the recess shown in FIG. 1 is circular. The fit between the corresponding protrusion of elongate member may be a loose fit and spacers or a compound such as adhesive or bonding material, or the like, may be used to keep a uniform gap between the two elongate members, or to provide non-conductivity between the two elongate members.

As discussed above, in some embodiments, the size and structure of one or more of the joints between elongated structures can be engineered such that it has a relatively low capacitance in the environment in which they are intended for use. One example of one such embodiment is shown in FIG. 4. This embodiment includes a shaft 203, for example a shaft for a guidewire, including a first elongated member 205 and a second elongated member 206. The elongated member 205 is an elongate solid wire that has a distal portion 213 and a recess 219 formed in the distal portion. The elongated member 206 is an elongate solid wire having a narrowed proximal portion 223 that is adapted and configured to fit at least partially within the recess 219 in the distal end of the first portion 205. A relatively non-conductive adhesive or bonding material 222 is disposed between the inner surface of the recess 219 and the outer surface of the proximal portion 223 of the elongated member 206 to provide a relatively low conductive joint 220 between two elongate members 205 and 206. An insulating layer or coating 241, for example PTFE, is disposed over the shaft 203. In this example, the relative dielectric constant of the adhesive material is about 2, and the thickness of the adhesive material is about 0.003 inches. The length 233 indicates the length of the overlap between the two elongated members, which in this example is about five millimeters. The outer diameter 235 of the narrowed proximal portion 223 is about 0.004 inches, and the outer diameter of both the first and second elongated members 205 and 206 is about 0.014 inches. The inner diameter 234 of the recess 219 is about 0.010. The capacitance of the inner was calculated to be about $5.994 \times 10^{-4}$ Pico Farad, the capacitance of the outer was calculated to be about $5.994 \times 10^{-4}$ Pico Farad, and the capacitance for concentric cylinders was calculated to be about 0.303 Pico Farad. Therefore, total calculated capacitance for this structure is calculated to be about 0.305 Pico Farad. Additionally, under the influence of radio waves generated by an MRI machine having a frequency of about 64 Mhz, the reactance of an ideal capacitor was calculated for this structure to be about $8.163 \times 10^{3}$ Ohms. The relatively high reactance indicates the structures ability to reduce resonance. It should be understood that the above description of sizes and properties is for one particular example embodiment, and is provided as merely one illustrative embodiment, and that the invention is not limited to this particular example.

In some embodiments, it may be necessary to consider the fringe fields that may be generated and extend beyond the joint to surrounding media in which the medical device is being used. For example, due to the relatively high dielectric constant of at least some tissue, such fringe fields may extend into the surrounding tissue in which the medical device is being used, and may increase the capacitance. If necessary, the medical device or the joint can be engineered to address these concerns. For example, a shielding layer of conductive material could be included on the device to confine the electric field.

For example, refer now to FIG. 5, which shows a shaft 303, for example a shaft for a guidewire, that is very similar to that shown in FIG. 4. The shaft 303 includes a first elongated member 305 and a second elongated member 306. The elongated member 305 is an elongate solid wire that has a distal portion 313 and a recess 319 formed in the distal portion. The elongated member 306 is an elongate solid wire having a narrowed proximal portion 323 that is adapted and configured to fit at least partially within the recess 319 in the distal end of the first portion 305. A relatively non-conductive adhesive or bonding material 322 is disposed between the inner surface of the recess 318 and the outer surface of the proximal portion 323 of the elongated member 306 to provide a relatively low conductive joint 320 between two elongate members 305 and 306. An insulating layer or coating 341, for example PTFE, is disposed over the shaft. A very thin shielding layer 350 made of a conductive material is disposed over the insulating layer or coating 341 about the joint 320. The shielding layer 350 can be made from a relatively conductive material such as gold, silver, copper, platinum, and the like, or combinations or mixtures thereof. The shielding layer 350 can be very thin, for example, in the range of about 1 to about 50 microns thick, and can be flexible such that it has minimal effect on the properties of the shaft. The shielding layer 350 can act to confine the electric field, for example, within the insulating layer or coating 341. Alternatively, other structures may be used to create the shielding layer 350, for example, a coiled wire or ribbon, a slotted or unslotted hypotube, or the like or other such structures.

In some embodiments, it may be desirable that the connection mechanism for connecting two elongated members permits flexibility while maintaining pushability and torqueability. For example, in some embodiments, it may be desirable that the connection mechanism allows the two elongated members to selectively pivot or bend in one or more directions relative to one another along their longitudinal axis. Additionally, in some embodiments, the pivoting or bending characteristics of connection mechanisms between multiple elongated members along the length of a shaft created thereby can vary to create desired flexibility and other characteristics. For example, in some embodiments, it may be desirable to alter the pivoting or bending direction of every next, or every other, or every third, etc. . . . connection mechanism to allow for desired pivotability and/or bendability. For example, in some embodiments, a first connection mechanism may allow for pivoting or bending of a first and second elongated members relative to the longitudinal axis in a first direction, and a next connection mechanism in a sequence of connection mechanisms may allow for pivoting or bending of second and third elongated members relative to the longitudinal axis in a second direction that is offset from the first direction. The first and second directions of pivoting or bending can be the same or offset in any desired amount to achieve the desired characteristics, and in some embodiments, can be offset in the range of about 1 to about 180 degrees about the longitudinal axis.

For example, refer now to FIG. 6, which shows two elongated segments 402 that can be connected in such a manner. In this embodiment, two or more elongated segments 402 can be connected in a hinge like relationship. Each of the segments 402 may include male end 404 and female end 406 that are configured for connection to one another for selective pivotal movement in one or more directions relative to the longitudinal axis of the shaft about the connection. Male end 404 of each segment is shaped and sized to permit insertion of it into the female end 406 of an adjacent segment. Male end 404 is generally sized in relation to the female end of the adjacent segment to permit a desired amount of pivotal movement of one segment 402 with respect to the other segment 402 along its longitudinal axis. If torqueability is desired, segments 402 may be connected using pins 412 disposed on male end 404 and holes 414 disposed in female end 408, or may be connected using some other suitable method. Pins 412 are generally disposed opposite each other to provide an axis of rotation for the joint. Holes 414 are positioned to receive pins 412. Pins 412 may have a beveled outer surface 416 to permit the segments 402 to snap together. Once connected together, the two connected segments 402 can pivot in relation to one another about the pivotal axis defined by the pins and holes. On each segment, the holes 414 may be rotationally offset from pins 412, for example in a plane in the range of about 70 to about 90 degrees from the plane of pins 412, to provide for multi-axial flexibility if a series of more than two such segments are connected together. In other embodiments, the holes 414 may be rotationally offset from pins 412 at a greater or lesser degree, as desired, for example, to provide the desired degree of flexibility. Alternatively, the holes and pins of particular segment or in a particular series of segments may not be offset or may be offset according to a particular design to provide for uni-axial or directional flexibility. Segments 402 may include lumens 420 to meet particular engineering, manufacturing or design requirements, if desired. In other embodiments, the segments 402 may be generally solid in cross section, but include openings in the female end adapted to receive the make end. The segments 402 shown are generally circular in cross sectional shape, but in other embodiments, other geometries, such as oval, triangular, square, multisides, or other such cross-sectional geometries can be used. Of course, other configurations are contemplated. For instance, pins 412 may be replaced by holes and a separate pin may be driven through these holes and holes 414 to fasten two segments together.

In the segments 402 shown, each segment 402 includes a male end 404 and a female end 406 such that each segment is adapted such that it can be connected to two other adjacent segments to form a series of segments. Two or more of such segments 402 can be connected together as described to form a shaft, or other portion of a medical device such as a guidewire or the like. Of course, each of the segments, such as a distalmost or proximalmost segment in a series of two or more may include an end, other than the male end or female end, which is suitable for use as an end of the assembly or device, or for connecting to another section of the medical device or guidewire. Each of the segments can include or be made of materials similar to those discussed above in reference to other embodiments.

Refer now to FIG. 7, which shows a series of segments 402 similar to those described with respect to FIG. 6 that are connected together as described, for example, to form a portion of a medical device shaft 401. The holes 414 and pins 412 in the ends of each segments 402 are offset in the range of about 90 degrees from each other to provide multi-axial flexibility or piviotability. In other embodiments, the holes 414 may be rotationally offset from pins 412 at a greater or lesser degree, for example, in the range of about 70 to about 120 degreed, or greater or lesser, for example, to provide the desired degree of flexibility. The length of each individual segment 402 can vary greatly and each of the segments 402 may be the same length or may be different lengths to provide the desired flexibility, MRI compatibility, and other characteristics. In some example embodiments, each of the segments 402 can have a length in the range of about 0.01 inch up to about one half the wavelength of an MRI field to which the structure will be exposed, or greater, depending upon the desired characteristics. In some embodiments, each segment 402 can have a length in the range of about 0.01 to about 1 inch, or in some embodiments, in the range of about 0.01 to about 0.25 inch. Additionally, the outer diameter of each individual segment 402 can vary greatly and each of the segments 402 may have the same diameter, or may have different diameters, to provide the desired characteristics. Additionally, the diameter of each segment may be constant, or may vary along the length thereof in a tapering or stepwise fashion. In some embodiments, the outer diameter of the each segment 402 can be in the range of about 0.005 to about 0.1 inch, or greater, and in some embodiments, in the range of about 0.008 to about 0.02 inch.

In some embodiments, to provide MRI compatibility, if desired, a number of approaches may be used including those discussed above with regard to other embodiments and others. For instance, all segments 402 may be made from a material that has a low conductivity or is non-conductive, or is MRI compatible. In some other embodiments, some of the segments 402 may be conductive, while one or more other segments may be made from a material that has a low conductivity or is non-conductive. The low or non-conductive segments could then be positioned within the series of segments to interrupt current flow such that no conductive path exists among the series of segments that is more than half the wavelength used by a particular MRI machine. For example, every other segment, every third segment, every fourth segment, etc. may be made from a material having no or a low conductivity. In such embodiments, a non-conductive segment or series of segments can be considered to be a connector mechanism or joint that provides a relatively non-conductive joint between two conductive segments or series of segments.

In yet another alternative, an insulative insert may prevent contact between the male end of one joint and the female end of another, with the fastening pin also made from a low or non-conductive material. Suitable materials that are non-conductive or have low conductivity include polymers and ceramics, or other such material, for example, those described above.

Figure 8:
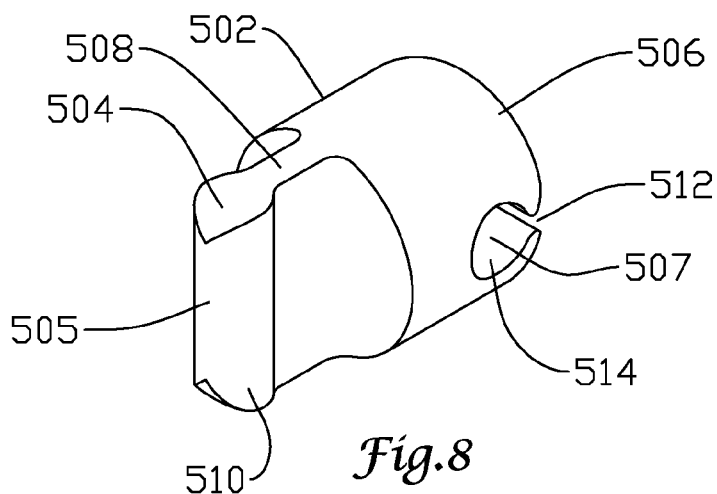
FIG. 8 is a perspective view of another example embodiment of a segment that may be used to connect to other segments in a medical device.

FIG. 8 is a perspective view of another example embodiment of a segment 502 that can be interconnected with other segments for form a portion of a medical device. The segment 502 has a male end 504 including a protrusion 505, and a female end 506 including a recess 507 defined therein. The protrusion 505 can be adapted and/or configured to fit within the recess 507 of an adjacent segment to interconnect to an adjacent segment. For example, in the embodiment shown, the recess 507 includes a narrowed neck portion 512 and a widened head portion 514, and the protrusion includes a narrow neck portion 508 and a widened head portion 510 that is adapted to slide within an adjacent recess 507. Such protrusions and recesses can be sized appropriately, for example, depending upon the size of the device being created, and/or the desired characteristics of the joints. Male end 504 and female end 506 may be rotationally offset to provide for multi-axial flexibility. Alternatively, male end 504 and female end 506 may be aligned or selectively offset to provide for directional flexibility.

Figure 9:
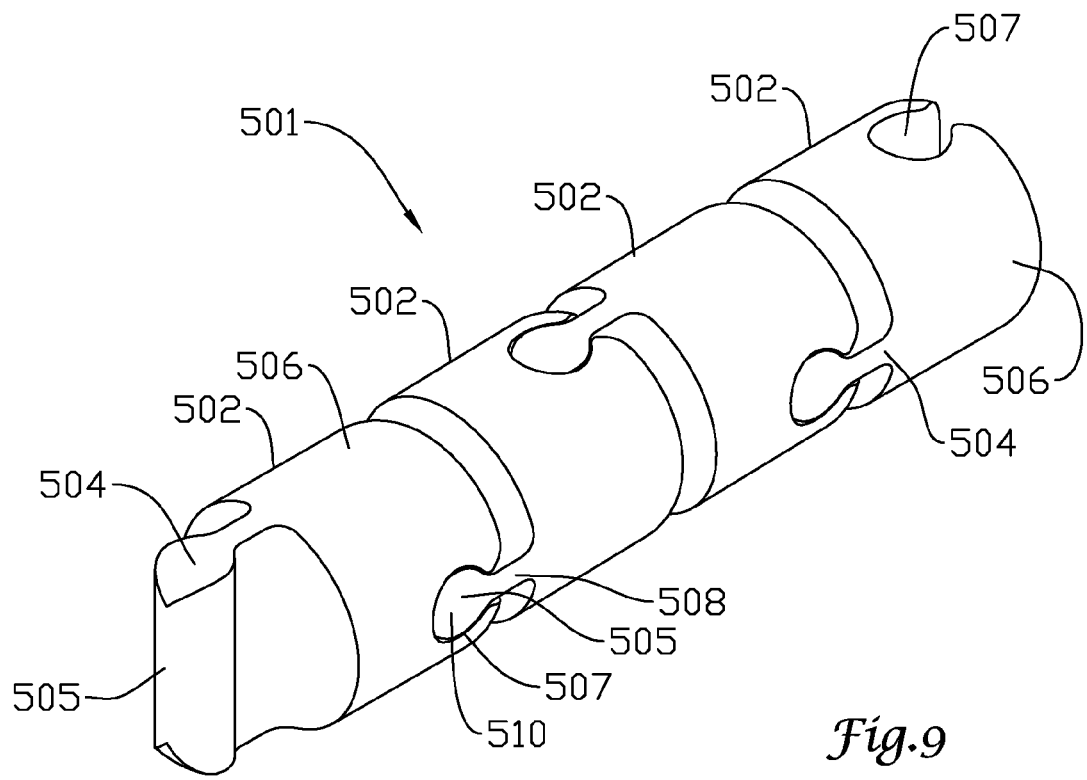
FIG. 9 is a perspective view of an example embodiment of a part of a medical device including a plurality of elongated segments as shown in FIG. 8 that are connected together.

As suggested above, a plurality of such segments 502 may be interlocked to form a medical device portion 501 as shown in FIG. 9. In some embodiments, the segments may be further retained in place relative to one another using additional structure or techniques. For example, additional structure, such as a sleeve or jacket, for example a polymer sleeve may be disposed over the joints (not shown) or by swaging the female end (the male end may be tapered inwards as shown for this purpose) or by some other suitable means. Additionally, each of the segments 502 can have a wide variety of lengths and diameters, for example, the example lengths and diameters as discussed above with regard to segments 402.

The medical device portion 501 may be made MRI compatible, if desired, by use of one or more of the techniques and materials discussed above; for example, selecting appropriate segment lengths, the use of non-conduction materials in some or all the joints, the use of spacing or inserts to interrupt conductivity, or by positioning non-conductive segments between conductive segments to interrupt current flow such that no conductive path exists among the series of segments that is more than half the wavelength used by a particular MRI machine.

Figure 10:
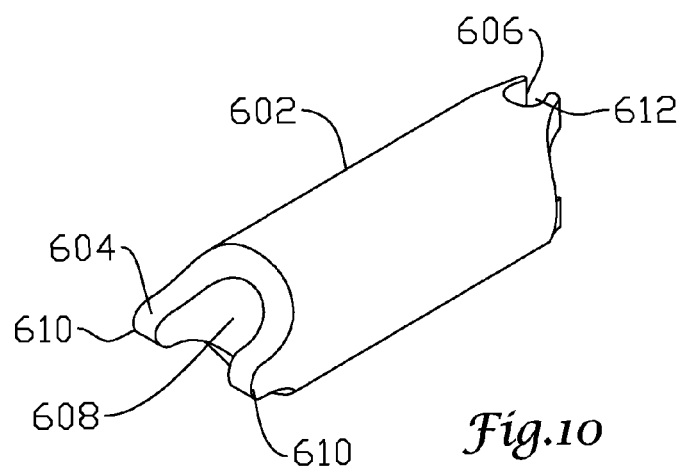
FIG. 10 is a perspective view of another example embodiment of a segment that may be used in a medical device having joints.
Figure 11:
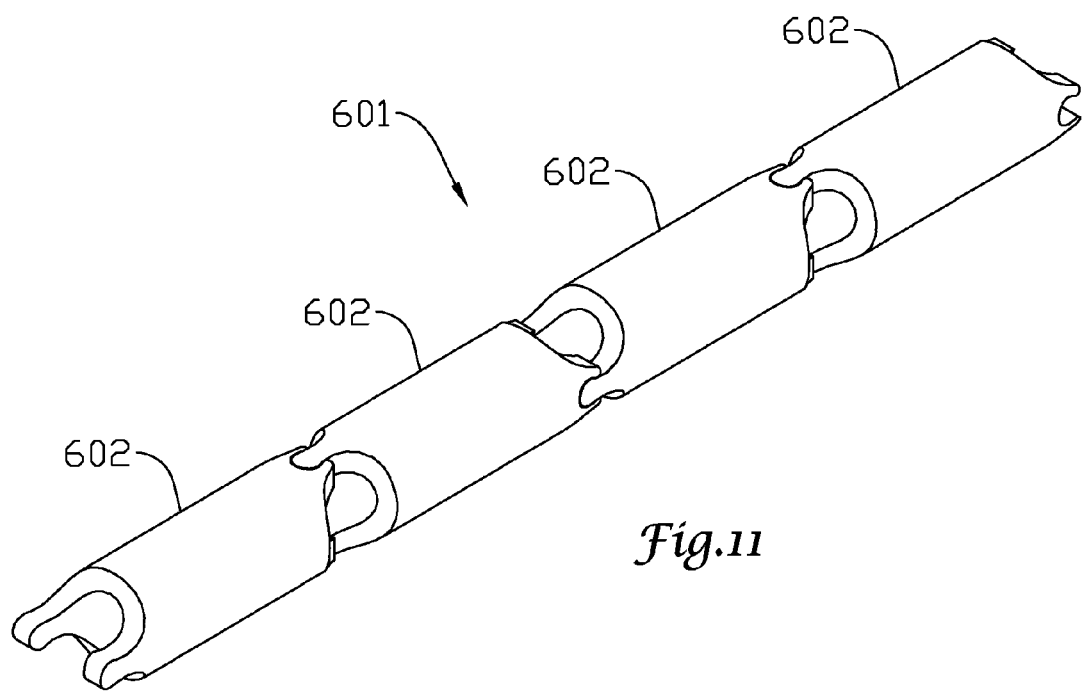
FIG. 11 is a perspective view of an example embodiment of a part of a medical device including a plurality of elongated segments as shown in FIG. 10 that are connected together.

FIG. 10 is a perspective view of another example embodiment of a segment 602 that can be interconnected with other segments to form a portion of a medical device. The segment 602 can be a generally tubular member that includes a male end 604, a female end 606, and a lumen 608. Male ends 604 comprise lobes 610 and female ends 606 comprise recesses 612. Lobes 610 may be symmetrically disposed about a central plane and the mating surfaces of each lobe may have a curved or non-parallel shape which fits into a corresponding curved or non-parallel shape in recesses 612, thus preventing sideways movement. Ends 604 and 606 may be offset as shown to provide multi-axial flexibility, if desired. A plurality of such segment 602 may be interlocked to form a medical device 601 as shown in FIG. 11. The segments 602 may be retained in place through the use of a sleeve externally or internally or by shaping the walls of male ends 604 and female ends 606 as discussed above. Medical device 601 may be made MRI compatible, if desired, by use of one or more of the techniques and materials described above. Additionally, each of the segments 602 can have a wide variety of lengths and diameters, for example, the example lengths and diameters as discussed above with regard to segments 402.

Refer now to FIG. 12, which is a cross sectional partial side view of another example embodiment of a guidewire 700 including an elongated proximal shaft 703 having a distal end portion 707 and a distal guidewire section 709 that includes a plurality of segments 702 that are essentially the same as segments 502 discussed above in relation to FIGS. 8 and 9. The segments 702 are interconnected, as described above, to form the distal guidewire section 709. The proximal most segment 702 can be attached to the distal end portion 707 using any suitable attachment technique, for example, the attachment techniques described above. In some example embodiments, the attachment can be made using a technique or material that provides a relatively non-conductive connection, as described above. The guidewire 700 can also include other structure, for example structure such as an outer coil 710, an inner coil 712, a safety or shaping ribbon 714, and a distal tip member 716 or other structure known for use in a guidewire. Such structures can be incorporated into the guidewire construction as is generally known, and can include materials, or be imparted with structure that provides a degree of MRI compatibility, as discussed above. Some examples of structure, materials, and techniques of guidewire constructions are disclosed in U.S. patent application Ser. Nos. 09/972,276, and 10/086,992, which are incorporated herein by reference.

Refer now to FIG. 13, which is a cross sectional partial side view of another example embodiment of a guidewire 800 including an elongated proximal shaft 803 having a distal portion 807 and a distal guidewire section 809 that includes a plurality of segments 802 that are essentially the same as segments 402 discussed above in relation to FIGS. 6 and 7. The segments 802 are interconnected, as described above, to form the distal guidewire section 809 defining a lumen 820 extending there through. The proximal most segment 802 can be attached to the distal portion 807 using any suitable attachment technique, for example, the attachment techniques described above. In some embodiments, the attachment can be made using a technique or material that provides a relatively non-conductive connection, as described above. Additionally, the distal portion 807 of the shaft can extend through the lumen 820, as shown. The guidewire 800 can also include other structure, for example structure such as an outer coil 810, an inner coil 812, a safety or shaping ribbon 814, and a distal tip member 816, or other structure known for use in a guidewire. Such structures can be incorporated into the guidewire construction as is generally known, and can include materials, or be imparted with structure that provides a degree of MRI compatibility, as discussed above. Again, some examples of structure, materials, and techniques of guidewire constructions are disclosed in U.S. patent application Ser. Nos. 09/972,276, and 10/086,992, which are incorporated herein by reference.

Figure 14:
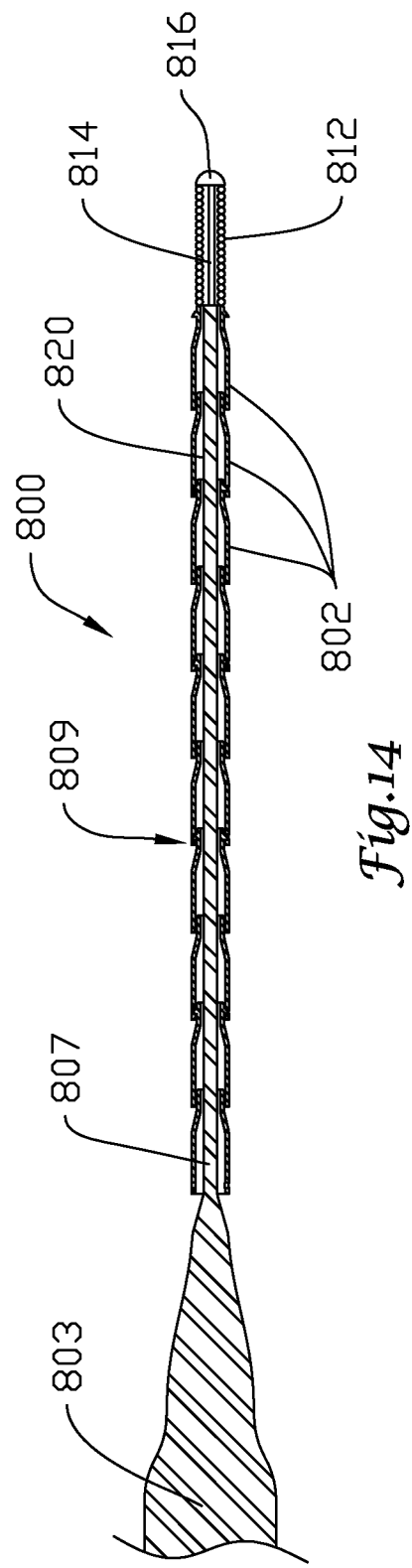
FIG. 14 is a cross-sectional schematic view of another example embodiment of a guidewire including a distal portion that includes a plurality of segments as shown in FIG. 6 that are connected together.

Refer now to FIG. 14, which is a cross sectional partial side view of another example embodiment of a guidewire 800 similar to that shown in FIG. 13, wherein like reference numerals indicate similar structure. In FIG. 14, however, the outer coil is absent, and the distal tip member 816 is sized appropriately in the absence of the outer coil. It should be understood that this is only an example embodiment, and that other structure may be used.

Those of skill in the art and others will recognize that the materials, structure, and dimensions of the medical device, or sections thereof, are dictated primarily by the desired characteristics and function of the final medical device, and that any of a broad range of materials, structures, and dimensions can be used. It will be understood that this disclosure, in many respects, is only illustrative. Changes may be made in details, particularly in matters of shape, size, material, and arrangement of parts without exceeding the scope of the invention. Those skilled in the art will recognize that the invention may be manifested in a variety of forms other than the specific embodiments described and contemplated herein. Accordingly, departures in form and detail may be made without departing from the scope and spirit of the invention as described in the appended claims.

What is claimed is:

1. A medical device, comprising:
   a first elongate member having a solid cross section and having a proximal end and a distal end, the distal end defining a recess therein; and
   a second tubular elongate member defining a lumen therein and having a distal end and a proximal end, the proximal end adapted and configured to fit within the recess;
   a joint having low electrical conductivity relative to the elongate members, wherein the joint is situated between and adjoins the two elongate members;
   an outer sheath disposed over at least part of the first elongate member and at least part of the second elongate member; and
   a shielding layer disposed over the outer sheath and about the joint.

2. The medical device of claim 1, further comprising a third elongate member having distal and proximal ends, wherein the proximal end of the third member is disposed in part within the distal end of the lumen of the second member.

3. The medical device of claim 2, wherein at least half of the lumen defined by the second tubular member defines a space that is unfilled by the first and third elongate members.

4. The medical device of claim 1, wherein the shielding layer is configured to confine an electric field.

5. The medical device of claim 1, wherein the outer sheath comprises a polymer.

6. The medical device of claim 1, wherein the recess is a slot defined by two interior walls.

7. The medical device of claim 1, wherein the recess is a wedge shaped slot defined by two flat interior walls that at least partially face distally.

8. The medical device of claim 1, wherein the recess is a wedge shaped slot defined by two flat interior walls that at least partially face proximally.

9. The medical device of claim 1, wherein the recess is an aperture defined by a circular interior wall.

10. The medical device of claim 1, wherein the recess is an aperture defined by a polygonal interior wall.

11. The medical device of claim 1, wherein the recess is an aperture defined by the interior surfaces of two or more protrusions.

12. The medical device of claim 1, wherein the length of each of the two elongate members is less than one half the wavelength of the radio frequency pulse applied by the MRI machine.

13. The medical device of claim 1, wherein the first elongate member comprises a material having a high modulus of elasticity relative to the material of the second elongate member.

14. A guidewire, comprising:
    a first elongate member having a solid cross section and a recess defined by at least one interior wall of the first elongate member;
    a second elongate member defining a lumen therethrough and having an end portion, wherein the end portion is adapted and configured to fit within the recess;
    a third elongate member having a solid cross section and having distal and proximal ends, wherein at least a portion of the proximal end of the third elongate member fits within the lumen of the second elongate member;
    an outer sheath disposed over at least part of the first elongate member and at least part of the second elongate member; and
    a shielding layer disposed over at least a portion of the outer sheath.

15. The guidewire of claim 14, further comprising a joint having low electrical conductivity relative to the elongate members, wherein the joint is situated between and adjoins the first and second elongate members or the second and third elongate members.

16. The guidewire of claim 15, wherein the shielding layer is disposed over the joint.

17. The guidewire of claim 14, wherein the length of each of the elongate members is less than one half the wavelength of the radio frequency pulse applied by the MRI machine.

18. A guidewire, comprising:
    a first elongate member having a solid cross section and a recess defined by at least one interior wall of the first elongate member;
    a second elongate member having an end portion, wherein the end portion is adapted and configured to fit within the recess;
    a joint having low electrical conductivity relative to the elongate members, wherein the joint is situated between and adjoins the two elongate members;
    an outer sheath disposed over at least part of the first elongate member and at least part of the second elongate member; and
    a shielding layer configured to confine an electric field, the shielding layer disposed over at least a portion of the outer sheath and the joint;
    wherein the length of each of the two elongate members is less than one half the wavelength of the radio frequency pulse applied by the MRI machine.

19. The guidewire of claim 18, further including one or more additional elongate members connected to the first or second elongate member.

* * * * *